United States Patent
Young

(10) Patent No.: US 12,053,418 B2
(45) Date of Patent: Aug. 6, 2024

(54) GOGGLE STRAP RETENTION SYSTEM

(71) Applicant: 100% SPEEDLAB, LLC, San Diego, CA (US)

(72) Inventor: Michael D. Young, San Diego, CA (US)

(73) Assignee: 100% Speedlab, LLC, San Diego, CA (US)

( * ) Notice: Subject to any disclaimer, the term of this patent is extended or adjusted under 35 U.S.C. 154(b) by 0 days.

(21) Appl. No.: 18/353,677

(22) Filed: Jul. 17, 2023

(65) Prior Publication Data

US 2024/0050277 A1 Feb. 15, 2024

Related U.S. Application Data

(63) Continuation of application No. 17/139,907, filed on Dec. 31, 2020, now Pat. No. 11,701,259.

(Continued)

(51) Int. Cl.
*A61F 9/02* (2006.01)
*B29C 45/00* (2006.01)
(Continued)

(52) U.S. Cl.
CPC .............. *A61F 9/027* (2013.01); *B29C 45/00* (2013.01); *A42B 3/08* (2013.01); *A42B 3/185* (2013.01); *B29C 2045/0093* (2013.01); *B29C 2045/14524* (2013.01); *Y10T 29/49908* (2015.01); *Y10T 29/49922* (2015.01); *Y10T 29/49936* (2015.01); *Y10T 29/49947* (2015.01); *Y10T 29/4998* (2015.01)

(58) Field of Classification Search
CPC .............. A61F 9/027; Y10T 29/49947; Y10T 29/49908; Y10T 29/49922; Y10T 29/49936; A42B 3/185; A42B 3/08
See application file for complete search history.

(56) References Cited

U.S. PATENT DOCUMENTS 1,829,010 A * 10/1931 Malcom .................. A61F 9/027
    24/265 A
2,110,332 A * 3/1938 Kimball .................. A61F 9/028
    2/13

(Continued)

FOREIGN PATENT DOCUMENTS

CN 201188900 Y 2/2009
DE 3503393 A1 8/1986
(Continued)

*Primary Examiner* — Jermie E Cozart
(74) *Attorney, Agent, or Firm* — Kolitch Romano Dascenzo Gates LLC

(57) ABSTRACT

Goggles are described as including an outrigger, an elastic band, and one or more cages. The elastic band is coupled to the cage, which may then be disposed within an opening of the outrigger. Thus, the elastic band may be coupled to the outrigger and, accordingly, to the goggle frame, through cage. Such a configuration may allow for the elastic band to have a stronger and more compact coupling to the outrigger and/or goggle frame. The cage may comprise metal or another material stronger than the material of the goggle frame and/or the outrigger. Furthermore, the cage may be more compact (e.g., narrower) than a typical connection while maintaining or improving strength.

19 Claims, 13 Drawing Sheets

Related U.S. Application Data

(60) Provisional application No. 62/956,014, filed on Dec. 31, 2019.

(51) Int. Cl.
    *A42B 3/08*     (2006.01)
    *A42B 3/18*     (2006.01)
    *B29C 45/14*     (2006.01)

(56) References Cited

U.S. PATENT DOCUMENTS

| | | |
|---|---|---|
| 5,181,280 A | 1/1993 | Zachry, Jr. |
| 5,809,580 A | 9/1998 | Arnette |
| 2004/0134039 A1 | 7/2004 | Tracy |
| 2011/0197346 A1 | 8/2011 | Burchett |
| 2013/0097855 A1 | 4/2013 | Li |
| 2020/0306088 A1 | 10/2020 | Young |

FOREIGN PATENT DOCUMENTS

| | | |
|---|---|---|
| WO | WO2017069779 A1 | 4/2017 |
| WO | WO2017189130 A1 | 11/2017 |

\* cited by examiner

GOGGLE STRAP RETENTION SYSTEM

CROSS-REFERENCES

The following applications and materials are incorporated herein, in their entireties, for all purposes: U.S. Provisional Patent Application Ser. No. 62/956,014, filed Dec. 31, 2019, U.S. patent application Ser. No. 16/824,525, filed Mar. 19, 2020, and U.S. patent application Ser. No. 17/139,907 filed Dec. 31, 2020.

FIELD

This disclosure relates to systems and methods for goggles. More specifically, the disclosed embodiments relate to structures utilized to couple a goggle strap to a goggle frame.

INTRODUCTION

Sport goggles are worn by users for various sports or activities, such as motorsports, powersports, snow sports, watersports, biking, or the like, to protect wearers' eyes. A sport goggle may be held to the wearer's eyes through a strap. During activities, the goggle may receive forces from, for example, impacts that may stretch or otherwise impart a pulling force on the strap. Additionally, a wearer may remove the goggle by pulling on a frame of the goggle and, thus, stretch the strap. Accordingly, the strap must be secured to the goggle frame in a robust manner to avoid failure of the strap, frame, and/or mechanisms for coupling the strap and frame to each other when the strap is stretched.

Furthermore, sport goggles may be bulky. A bulky goggle may be heavy, may result in additional unwanted impacts, may be harder to wear, may reduce the field of vision of the wearer, and/or may be more difficult to handle in other ways. Thus, there is a need for improved sport goggles.

SUMMARY

The present disclosure provides systems, apparatuses, and methods relating to molded multi-component goggle outriggers and fastener systems for connecting elastic bands to the outriggers and/or goggle frame.

In some examples, a goggle includes an outrigger coupled to or part of a frame of the goggle, an elastic band configured to secure the goggle to a wearer's head, and a cage coupled to the elastic band and removably disposed within an opening of the outrigger, wherein the cage comprises a material having a higher modulus of elasticity than the material of the outrigger.

In some examples, a method for manufacturing a sport goggle includes: molding a first segment of an outrigger such that an end portion of the first segment includes a joint feature; and molding a second segment of the outrigger onto the first segment by flowing molten material into contact with the joint feature, such that a permanent joint is automatically formed between the first segment and the second segment.

In some examples, a method for manufacturing a sport goggle includes: injection molding a first segment of an outrigger of a goggle; and injection molding a second segment of the outrigger by flowing molten material into contact with an end of the first segment, such that a fixed joint is automatically formed at a junction between the first and second segments; wherein the end-to-end first and second segments combine to extend an entire length of the outrigger.

Features, functions, and advantages may be achieved independently in various embodiments of the present disclosure, or may be combined in yet other embodiments, further details of which can be seen with reference to the following description and drawings.

DETAILED DESCRIPTION

Figure 1:
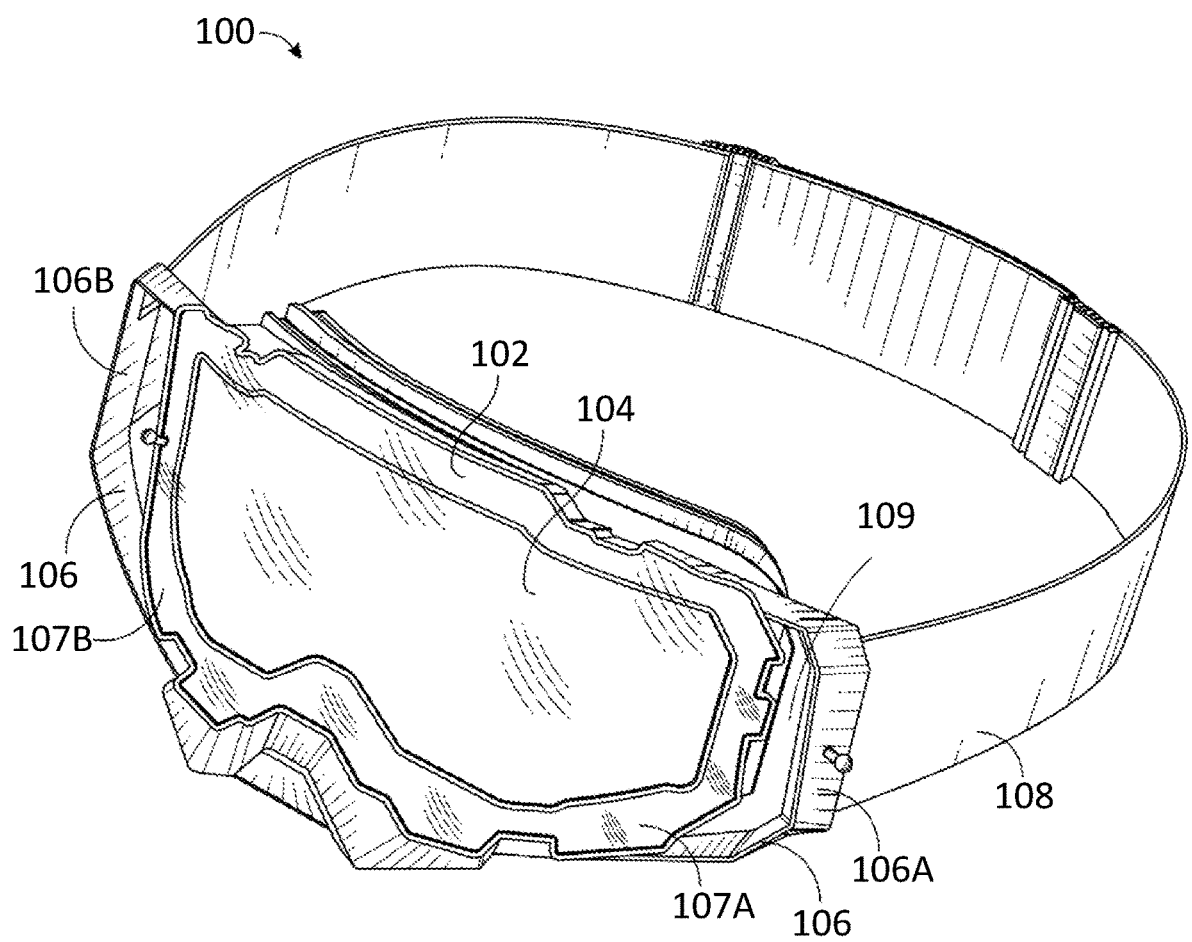
FIG. 1 is an isometric view of a first illustrative goggle in accordance with aspects of the present disclosure.

Various aspects and examples of a molded multi-component goggle outrigger, as well as related systems and methods, are described below and illustrated in the associated drawings. Unless otherwise specified, a goggle outrigger in accordance with the present teachings, and/or its various components, may contain at least one of the structures, components, functionalities, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses.

Additionally, the advantages provided by the examples and embodiments described below are illustrative in nature and not all examples and embodiments provide the same advantages or the same degree of advantages.

This Detailed Description includes the following sections, which follow immediately below: (1) Definitions; (2) Overview; (3) Examples, Components, and Alternatives; (4) Advantages, Features, and Benefits; and (5) Conclusion. The Examples, Components, and Alternatives section is further divided into subsections, each of which is labeled accordingly.

Definitions

The following definitions apply herein, unless otherwise indicated.

"Comprising," "including," and "having" (and conjugations thereof) are used interchangeably to mean including but not necessarily limited to, and are open-ended terms not intended to exclude additional, unrecited elements or method steps.

Terms such as "first", "second", and "third" are used to distinguish or identify various members of a group, or the like, and are not intended to show serial or numerical limitation.

"AKA" means "also known as," and may be used to indicate an alternative or corresponding term for a given element or elements.

"Elongate" or "elongated" refers to an object or aperture that has a length greater than its own width, although the width need not be uniform. For example, an elongate slot may be elliptical or stadium-shaped, and an elongate candlestick may have a height greater than its tapering diameter. As a negative example, a circular aperture would not be considered an elongate aperture.

"Coupled" means connected, either permanently or releasably, whether directly or indirectly through intervening components.

"Resilient" describes a material or structure configured to respond to normal operating loads (e.g., when compressed) by deforming elastically and returning to an original shape or position when unloaded.

"Rigid" describes a material or structure configured to be stiff, non-deformable, or substantially lacking in flexibility under normal operating conditions.

"Elastic" describes a material or structure configured to spontaneously resume its former shape after being stretched or expanded.

Directional terms such as "up," "down," "vertical," "horizontal," and the like should be understood in the context of the particular object in question. For example, an object may be oriented around defined X, Y, and Z axes. In those examples, the X-Y plane will define horizontal, with up being defined as the positive Z direction and down being defined as the negative Z direction.

"Providing," in the context of a method, may include receiving, obtaining, purchasing, manufacturing, generating, processing, preprocessing, and/or the like, such that the object or material provided is in a state and configuration for other steps to be carried out.

In this disclosure, one or more publications, patents, and/or patent applications may be incorporated by reference. However, such material is only incorporated to the extent that no conflict exists between the incorporated material and the statements and drawings set forth herein. In the event of any such conflict, including any conflict in terminology, the present disclosure is controlling.

Overview

In general, a goggle in accordance with the present teachings may include a multi-component outrigger system coupled to each side (e.g., lateral ends) of the goggle frame. An elastic band of the goggle may be coupled to the goggle by way of the outrigger system, and configured to retain the goggle against the head of a wearer. The outrigger system includes a pair of outriggers, each of which is a generally horseshoe- or C-shaped structure extending outward from one side of the frame of the goggle, such that a gap is formed between a middle portion of the outrigger and the rest of the frame. Outriggers of the present disclosure include a first segment and a second segment permanently secured together, e.g., end-to-end, such that the outrigger extends continuously from the first segment to the second segment. In some examples, the end-to-end first and second segments combine to extend an entire length of the outrigger. In some examples, the first segment extends along and defines a first portion of an arc of the C-shape, and the second segment extends along and defines a remaining portion of the C-shape. In some examples, a junction between the first segment and the second segment is disposed at or near a corner area (e.g., a lower corner) of the outrigger. The first segment may have a first material characteristic, and the second segment may have a second (e.g., different) material characteristic. The first and second material characteristics may comprise any suitable distinguishing feature, such as a material type, a material color, a material texture, and/or the like. However, it is noted that mere color combinations of any kind would be purely ornamental in nature. The first and second segments may include complementary shapes configured to secure the first and second segments together. The complementary shapes may create a solid friction lock securing the first and second segments together. The second segment may be molded onto or into the first segment, thereby fixing the first and second segments together permanently, e.g., with a mechanical and/or chemical bond.

According to another aspect of the present disclosure, a method of manufacturing a goggle may include forming the first segment of the outrigger, and forming the second segment of the outrigger such that the second segment is joined to at least a portion of the first segment (e.g., mechanically joined, chemically bonded, etc.) to secure the first and second segments together. In some examples, forming the second segment such that the second segment is joined to at least a portion of the first segment may include forming (e.g., injection molding) the second segment onto and/or into the first segment to mechanically and/or chemically lock the first and second segments together. The segments are attachable to a goggle frame, e.g., by way of friction-fit tabs and slots. In some examples, the first segment is formed as a single piece with the goggle frame. In some examples, the second segment is formed as a single piece with the goggle frame.

The first segment of the outrigger may be manufactured to include features for complementary material flow of the second segment therein or thereon during the molding process, to secure the second segment to the first segment. In some examples, these features include one or more protrusions, recesses, pores, apertures, channels, and/or the like. In some embodiments, forming the second segment of the outrigger includes flowing material of the second segment through, into, and/or around at least a portion of the first segment to mechanically lock the first and second segments together. A first material characteristic or property of the first segment may be different than a second material characteristic or property of the second segment. For example, the two segments may be different materials, have different material textures, hardnesses, surface finishes, colors, toughnesses, elasticities, and/or the like.

According to another aspect of the present disclosure, a goggle may include a goggle frame, a first outrigger coupled to a first end of the goggle frame, a second outrigger coupled to a second end of the goggle frame, an elastic band, and a first cage and second cage disposed on the ends of the band. Each of the outriggers may respectively include an opening or recess configured to removably receive the cages of the band. Each of the first and second cages may include a band opening and at least one protrusion disposed within the band opening. The band opening of the first cage may receive the first end of the elastic band. The band opening of the second cage may receive the second end of the elastic band. The at least one protrusion of each of the first cage and the second cage may be coupled to the elastic band to hold the elastic band within the respective band opening. In some examples, the cages are molded onto the elastic bands, such as by an over-molding process.

In some examples, the first cage and the second cage each may further include a first cage fastener opening, the elastic band may include a first band fastener opening, and the goggle may further include a first fastener configured to be disposed through both the first cage fastener opening and the first band fastener opening. In a certain such example, each of the first cage and the second cage may further include a second cage fastener opening, the elastic band may further include a second band fastener opening, the goggle may further include a second fastener configured to be disposed through both the second cage fastener opening and the second band fastener opening, and the first cage fastener opening and the second cage fastener opening may be disposed on opposing sides of the cage. In some examples, the first fastener and the second fastener may each comprise a removable fastener, such as a brad, screw, pin, and/or the like.

In some examples, each of the first cage and the second cage may further include a detent, and each of the first outrigger and the second outrigger may further include a depression disposed within each of the respective first and second outrigger openings and configured to receive the detent to hold the respective cage within the respective outrigger opening.

In some examples, the goggle may further include a goggle lens disposed within the goggle frame.

In some examples, the first cage and/or the second cage comprise a metallic material. In some examples, at least one of the protrusions is shaped to retain the elastic band within the cage, such as a protrusion that is triangular, pyramidal, serrated, jagged, and/or the like. In some examples, at least one of the protrusions is a substantially triangular shaped tooth. In some examples, the elastic band opening includes a substantially rectangular cross section. At least one of the protrusions may extend into the substantially rectangular cross section.

According to another aspect of the present disclosure, a method of manufacturing the goggle may include forming the goggle frame, forming the first cage, forming the second cage, disposing the first cage within the first outrigger opening, and disposing the second cage within the second outrigger opening. In a certain such examples, the first outrigger and the second outrigger may be formed with the goggle frame (e.g., as a single piece). In some examples, the method may further include forming the first outrigger, forming the second outrigger, and coupling the first outrigger and the second outrigger to the goggle frame. In a certain additional such embodiment, forming the first cage may include disposing the first end of the elastic band within the band opening of the first cage, and forming the second cage may include disposing the second end of the elastic band within the band opening of the second cage.

According to another aspect of the present disclosure, a method of using the goggle may include receiving a force on the elastic band, stretching the elastic band due to the force, and holding the first end and the second end of the elastic band within the respective band openings, against the force.

According to another aspect of the present disclosure, a cage may be configured to be disposed within a portion of a goggle frame. The cage may include a cage body configured to be disposed within an opening of a goggle frame, a band opening disposed within the cage body and configured to receive an elastic band, and a protrusion disposed within the band opening and configured to couple to the elastic band to hold the elastic band within the band opening.

In some examples, the cage may further include a first cage fastener opening configured to receive a first fastener. In a certain such embodiment, the cage may further include a second cage fastener opening configured to receive a second fastener, where the first cage fastener opening and the second cage fastener opening may be disposed on opposing sides of the cage. In a certain additional such embodiment, the cage body may include a detent configured to be disposed within a depression of the goggle frame. In a certain additional such embodiment, the cage body may be metal, the protrusion may be a substantially triangular shaped tooth, the band opening may include a substantially rectangular cross section, and the protrusion may protrude into the substantially rectangular cross section. In a certain additional such example, the cage body may include a first portion and a second portion coupled to the first portion.

According to another aspect of the present disclosure, a method of manufacturing the cage may include forming the cage body and forming the protrusion. In a certain such embodiment, the cage body and the protrusion may be formed by machining a metal stock. In a certain additional such examples, forming the cage body may include forming the cage body from sheet metal to define the band opening and forming the protrusion may include bending the protrusion into the band opening. In a certain additional such embodiment, the cage body and the protrusion may be formed by three-dimensional printing.

Examples, Components, and Alternatives The following sections describe selected aspects of illustrative goggles as well as related systems and/or methods. The examples in these sections are intended for illustration and should not be interpreted as limiting the scope of the present disclosure.

Each section may include one or more distinct embodiments or examples, and/or contextual or related information, function, and/or structure.

A. Illustrative Goggles

A goggle that includes a multi-component outrigger is described herein. The systems and methods described herein allow an outrigger of the goggle to be formed of two or more elements or pieces, such as a first segment and a second segment, secured together. Portions of the first segment may interlock or join with complementary portions of the second segment, such as through interlocking shapes, a solid friction lock, molding, bonding, etc. The joining portions of the first and second segments may include complementary shapes that interlock together, whether permanently or otherwise, to secure the first and second segments together. The second segment may be molded to or around at least a portion of the first segment, or vice versa, to secure the first and second segments together. One segment may be formed with interlocking features such that material flow therein, thereover, or therethrough of a subsequently formed segment will mechanically join and/or chemically bond the segments together.

An elastic strap of the goggle may be secured to each outrigger. For example, the elastic strap may be coupled to the goggle (e.g., to the outrigger or goggle frame) using a cage that offers a smaller form factor and a stronger connection. The outrigger includes an opening configured to receive and retain the cage. The cage may include a first opening configured to receive the elastic band and a protrusion disposed within the first opening and configured to couple to the elastic band to hold the elastic band within the first opening. Features within the opening of the cage in which the elastic strap is disposed may aid in the cage holding the elastic band. Features on the outside of the cage may aid in attaching the cage to the opening of the goggle frame and/or the outrigger.

Figure 2:
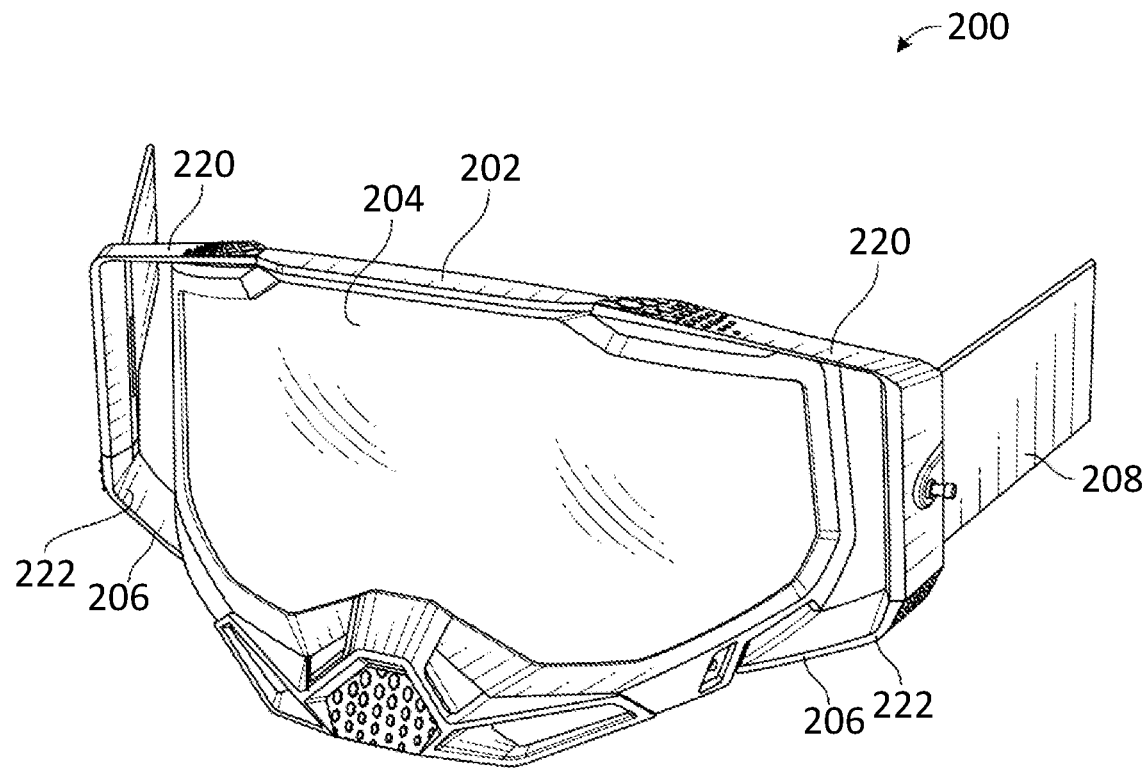
FIG. 2 is an isometric view of a second illustrative goggle in accordance with aspects of the present disclosure.

FIG. 1 is a perspective view of a goggle, in accordance with an embodiment of the present disclosure. FIG. 2 shows a perspective view of a goggle, in accordance with another embodiment of the present disclosure.

FIG. 1 illustrates a goggle 100 that includes a goggle frame 102, a goggle lens 104, an outrigger 106, and an elastic band 108. FIG. 2 illustrates a goggle 200 that includes a goggle frame 202, a goggle lens 204, an outrigger 206, and an elastic band 208. Except as otherwise described, goggle 200 of FIG. 2 is substantially similar to goggle 100 of FIG. 1. Therefore, like descriptions of goggle 200, including the goggle frame 202, goggle lens 204, outrigger 206, and elastic band 208, among others, may be omitted for ease of reference and brevity.

Goggle frame 102 is configured to receive goggle lens 104 within an aperture of the goggle frame. Goggle frame 102 may be made of any appropriate material, such as one or more of plastics, composites, metals, or other materials. Goggle frame 102 may be formed by, for example, molding, casting, machining, and/or coupling together (e.g., gluing or mechanically fastening) one or more of multiple components. Goggle frame 202 of goggle 200 is similar to goggle frame 102 of goggle 100.

In certain embodiments, goggle lens 104 is configured to be selectively decoupled from goggle frame 102, such as to facilitate replacement of goggle lens 104. Goggle lens 104 may include any suitable goggle lens that allows a wearer to view objects on the other side of the lens while protecting the wearer's eyes. Goggle lens 204 may be substantially similar to goggle lens 104.

Elastic band 108 is coupled to goggle frame 102. Elastic band 108 may be, for example, a strap that is configured to hold goggle 100 to the face of the wearer when in use. As such, elastic band 108 is configured to be stretched to conform with the wearer's head, to allow for goggle 100 to be disposed on the wearer's head, to allow for goggle 100 to be removed from the wearer's head, and/or for other reasons. Elastic band 108 may be adjustable in length to accommodate a variety of head sizes. Additionally, as described herein, elastic band 108 is coupled to one or more cages, and the cages are removably coupled to goggle frame 102 and/or outrigger 106. Elastic band 208 may be similar to elastic band 108.

Goggle frame 102 includes at least one outrigger 106 coupled to at least one end of the goggle frame. Outrigger 106 may be an integral extension of goggle frame 102. In some examples, outrigger 106 is separate from goggle frame 102 but coupled thereto. Thus, for example, outrigger 106 may be formed separately from goggle frame 102 and coupled to goggle frame 102 (e.g., mechanically, adhesively, or through another technique). In some examples, goggle 100 includes a pair of outriggers disposed on opposing lateral ends or sides of the goggle frame. For example, a first outrigger 106A may be disposed on a first end 107A of goggle frame 102 (e.g., the left side of goggle frame 102) and a second outrigger 106B may be disposed on a second end 107B of goggle frame 102 (e.g., the right side of goggle frame 102). As shown, the outriggers 106, 106A, 106B may loop away from goggle frame 102 to define a space 109 between the outriggers 106, 106A, 106B and the goggle frame 102. Depending on the application, the outriggers 106, 106A, 106B may form a closed loop with goggle frame 102, though other configurations are contemplated. The outriggers 206 of goggle 200 may be substantially similar to outriggers 106, 106A, 106B of goggle 100.

Each outrigger 106 is configured to attach elastic band 108 to goggle frame 102. For example, ends of elastic band 108 may be secured to first and second outriggers 106A, 106B. Elastic band 108 may be secured to the outriggers 106, 106A, 106B in many configurations. For instance, opposing ends of elastic band 108 may be coupled to the first and second outriggers 106A, 106B. In some embodiments, opposing ends of the elastic band 108 may be positioned at least partially within the space 109 between the outrigger 106 and the goggle frame 102 to secure elastic strap 108 to goggle frame 102. In some embodiments, the opposing ends of elastic band 108 may wrap around the outriggers 106, create an interference fit with the outriggers 106 (e.g., due to sewn bundles disposed at ends of the elastic band), be joined, bonded, or adhered to the outriggers 106, create a cooperative holding arrangement between the elastic band 108 and the outriggers 106, or the like, or any combination thereof. In some embodiments, each outrigger 106 may include an opening that receives a corresponding cage, as explained below. Each outrigger 206 of goggle 200 may be substantially similar to outriggers 106, 106A, 106B of goggle 100.

Figure 3:
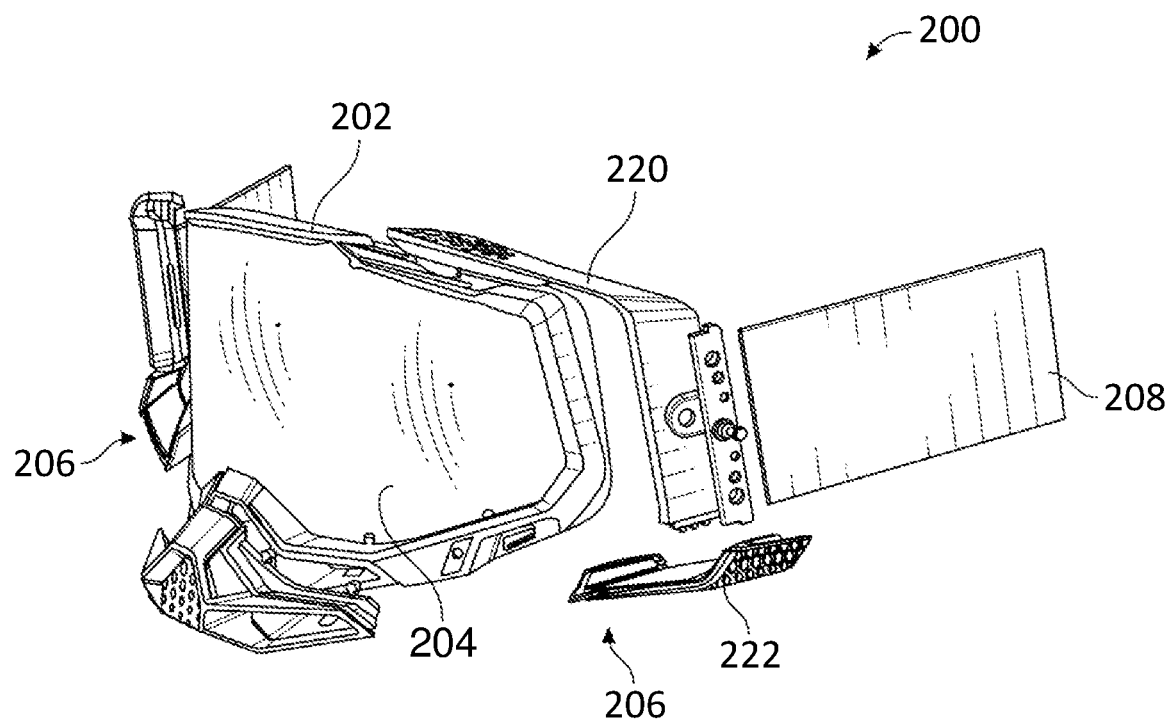
FIG. 3 is an exploded view of portions of the goggle of FIG. 2.
Figure 4:
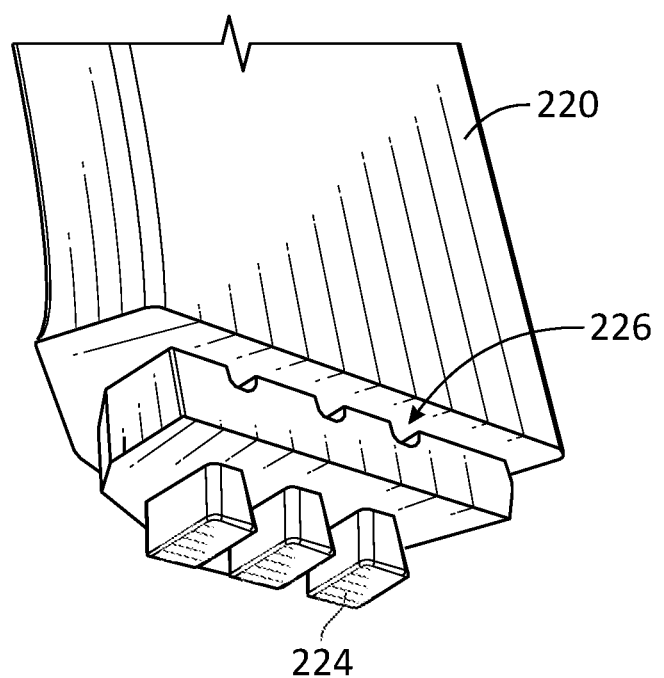
FIG. 4 is an isometric view of an outrigger interface of the goggle of FIG. 2.

FIG. 3 shows an exploded view of portions of goggle 200 of FIG. 2, in accordance with an embodiment of the present disclosure. FIG. 4 shows an enlarged, fragmentary view of portions of goggle 200 of FIG. 2, in accordance with an embodiment of the present disclosure. Referring to FIGS. 3-4, each outrigger 206 may include many configurations. For instance, outrigger 206 may be formed integrally with goggle frame 202 or may be a separate element connected to goggle frame 202. Depending on the application, each outrigger 206 may be formed from one or more elements or pieces. For example, as shown in FIGS. 3-4, each outrigger 206 may be formed from a plurality of components secured or formed together. Outriggers 106, 106A, 106B may be substantially identical to outriggers 206.

Each outrigger 206 may be a multi-piece outrigger assembly including at least a first segment 220 and a second segment 222 connected or formed together. In some examples, the first and second segments 220, 222 are secured or formed together by a mechanical joint. For instance, portions of the first segment 220 may interlock or join with complementary portions of the second segment 222, such as through interlocking shapes, a solid friction lock, and/or co-molding, over-molding, double shot molding, or the like. For example, the first and second segments 220, 222 may be secured together using joinery techniques, such as a dovetail joint or the like. In such examples, the joining portions of the first and second segments 220, 222 may include complementary shapes that interlock together, whether permanently or otherwise, to secure first segment 220 to second segment 222. In some examples, the shape and/or material properties of the complementary portions of the first and second segments 220, 222 may allow the first and second segments 220, 222 to be snapped or coupled together permanently.

In some examples, second segment 222 is molded to or around at least a portion of the first segment 220, or vice versa, to permanently secure the first and second segments 220, 222 together. In such examples, the segment which is formed first during the manufacturing process, such as the first segment 220, has interlocking features 224 such that material flow of the segment which is formed second during the manufacturing process, such as the second segment 222, will mechanically join the first and second segments 220, 222 together. For instance, the first segment may include one or more protrusions, tunnels, recesses, apertures, pores, and/or holes 226 in, around, or through which material of the second segment may flow during formation of the second segment, to permanently join first and second segments 220, 222 together. Such examples also facilitate attachment of first segment 220 to second segment 222 without inducing stress within each segment.

In such examples, each outrigger 206 may be formed from the same or different materials to achieve a desired functional or aesthetic configuration. For instance, the first segment 220 may be formed from a first material having a first material characteristic, and the second segment 222 may be formed from a second material having a second material characteristic. The first and second materials may be any suitable material. For example, the first segment 220 and/or the second segment 222 may be formed from polycarbonate, polyurethane (PU), polyethylene, polypropylene, polyvinyl chloride, thermoplastic polyurethane (TPU), acrylonitrile butadiene styrene (ABS), polycarbonate-ABS (PC-ABS), thermoplastic elastomers (TPE), aluminum, titanium, metallic materials, and/or a rubberized material, among others, or any combination thereof. In examples wherein one or more outrigger segments comprises a metal, the outrigger may have a slimmer profile than outriggers comprising only polymeric materials.

The first and second materials may be the same material or different materials. For example, both the first material and the second material may be a plastic material, both the first material and the second material may be a rubberized material, or one of the first material and the second material may be a plastic material with the other of the first material and the second material being a rubberized material. Some illustrative material combinations of the first and second materials include, without limitation (with the material combination listed as first material:second material): PC-ABS:PC-ABS, PC-ABS:TPE, TPE:PC-ABS, PC-ABS: TPU, TPU:PC-ABS, PU:PU, PU:TPE, TPE:PU, TPU:TPU, TPU:TPE, TPE:TPU, or TPE:TPE. Such material combinations are exemplary only and other material combinations are contemplated.

The first material characteristic may be any material property of the first material, such as a first color, strength, feel, texture, toughness, hardness, wear resistance, or other property of the first material. The second material characteristic may be any material property of the second material, such as a second color, strength, feel, texture, toughness, hardness, wear resistance, or other property of the second material. The first material characteristic may be the same as or different than the second material characteristic. For instance, the first and second materials may differ or be similar in color, strength, feel, texture, wear resistance, or other material properties. In some embodiments, the first material may have a first texture, and the second material may have a second texture. The first texture may be similar to identical to the second texture or the first texture may be different than the second texture to provide a desired texture combination of the first and second materials. Some possible texture combinations of the first and second materials may include, without limitation (with the texture combinations listed as first texture:second texture or second texture:first texture): smooth:smooth, rough:rough, rippled:rippled, bumpy:bumpy, ridged:ridged, smooth:rough, smooth: rippled, smooth:bumpy, smooth:ridged, bumpy:ridged, bumpy:rippled, bumpy:rough, rough:rippled, rough:ridged, rippled:ridged, first pattern:second pattern, or the like. Such texture combinations are exemplary only and other texture combinations are contemplated.

In some examples, the first material may have a first color, and the second material may have a second color, resulting in an ornamental appearance without requiring painting or other coloring methods. Depending on the application, the first color may be similar or identical to the second color or the first color may be different than the second color to provide a desired color combination of the first and second materials. The first color may be any shade of color, such as any shade of black, blue, brown, green, orange, red, white, yellow, cyan, gray, magenta, pink, purple, etc., or any combination thereof. The second color may be any shade of color, such as any shade of black, blue, brown, green, orange, red, white, yellow, cyan, gray, magenta, pink, purple, etc., or any combination thereof. Some possible color combinations of the first and second materials include, without limitation (with the color combination listed as first color:second color or second color:first color): black:black, blue:blue, green:green, orange:orange, red:red, white:white, yellow:yellow, cyan:cyan, gray:gray, purple:purple, black: gray, black:yellow, black:green, black:gold, blue:yellow, blue:red, red:orange, red:purple, white:black, white:blue, white:green, white:red, white:yellow, white:cyan, white:gray, white:purple, white:gold, gray:gold, cyan:green, or orange:brown, and any shades thereof. Such color combinations are exemplary only and other color combinations are contemplated.

In this manner, the outriggers 206 may be tailored to application, use, cost, aesthetic appeal, and/or the like. For instance, a goggle for use in snow sports may have an outrigger with different characteristics than a goggle for use in motorsports. Similarly, a google for use in motocross may require an outrigger with different characteristics than a goggle for supercross, road racing, or leisurely riding. A goggle intended for youth use may require an outrigger with different characteristics than a goggle intended for adult use. In such embodiments, the material properties of the first segment 220 and/or the second segment 222 may be chosen to tailor the goggle 200 to the particular application, sport, activity, or intended use.

Figure 5:
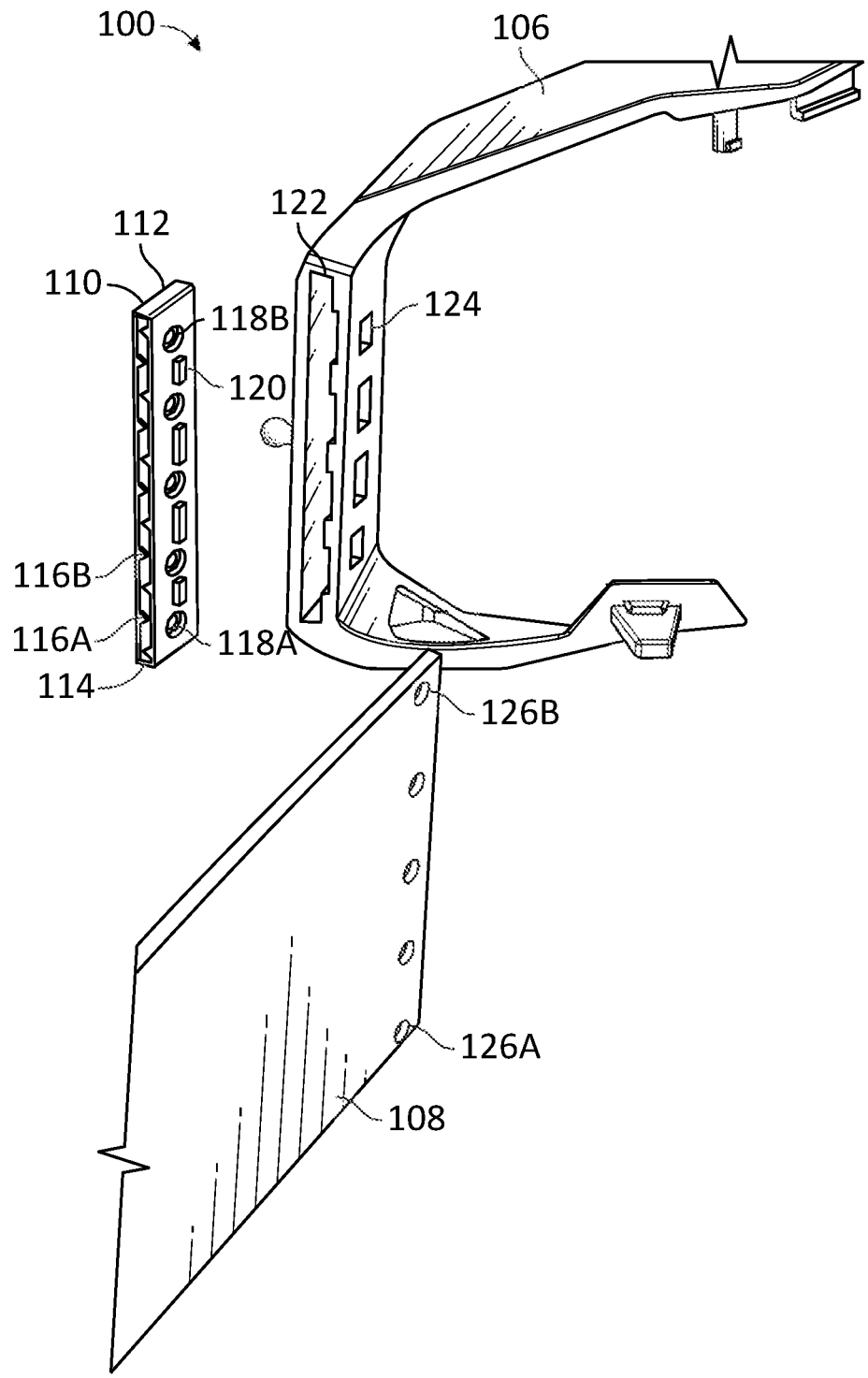
FIG. 5 is an exploded view of portions of an outrigger of the goggle of FIG. 1.

FIG. 5 shows an exploded view of portions of the goggle of FIG. 1, in accordance with an embodiment of the present disclosure. FIG. 5 illustrates an exploded view of goggle 100 of FIG. 1 that includes outrigger 106, elastic band 108, and a cage 110. Though the cage 110 is described herein with reference to the outrigger 106, in some embodiments, goggle frame 102 may not include an outrigger 106. In such embodiments, cage 110 described herein may be configured to be disposed within one or more openings of the goggle frame 102 itself. As such, the systems and techniques described herein is applicable to goggles that do not include outriggers as well as goggles that include outriggers. Additionally, cage 110 shown in and described with reference to FIGS. 5-14 may be implemented in goggle 200 of FIGS. 2-4. For instance, cage 110 may be associated with the first segment 220 and/or the second segment 222 similar to that described below. Thus, the description of FIGS. 5-14 will refer to the goggle 100 of FIG. 1 for ease of reference and brevity, only.

As shown in FIG. 5, elastic band 108 may be coupled to cage 110. The cage may then be disposed within an opening 122 of outrigger 106. Thus, elastic band 108 may be coupled to outrigger 106 and, accordingly, goggle frame 102, through cage 110. Such a configuration may allow for elastic band 108 to have a stronger and more compact coupling to outrigger 106 and/or goggle frame 102.

Cage 110 may comprise metal or another material stronger than the material of goggle frame 102 and/or the outrigger 106 (e.g., a modulus of elasticity of the material of cage 110 may be higher than the modulus of elasticity of the material of the goggle frame 102 and/or the outrigger 106). Thus, coupling the elastic band 108 to the cage 110 and then disposing the cage 110 within the opening 114 may lead to a stronger connection than typical techniques that attach the elastic band directly to the goggle frame and/or the outrigger.

Furthermore, cage 110 may be more compact (e.g., narrower) than a typical connection while maintaining or improving strength. Typical connections between goggles and elastic bands include an interference fit between a sewn bundle of material disposed at ends of an elastic band and an opening disposed within a goggle and/or outrigger. Additionally, a cage comprising metal or metallic materials may have a slimmer profile than cages comprising plastics, polymers, and/or the like. Thus, outrigger 106 and/or goggle frame 102 may be of a smaller size. As, typically, the elastic band 108 is coupled to the sides of goggle 100 (e.g., disposed to the left and right of the face of the wearer), such a configuration may lead to a more compact goggle frame 102 and/or more compact outrigger 106 that can improve the wearer's field of vision.

Cage 110 may include features for coupling to elastic band 108 and/or coupling to outrigger 106. For example, cage 110 may include a cage body 112. The cage body 112 may include an opening 114. The opening 114 may be substantially rectangular in cross section to receive elastic band 108. The opening 114 may be of a height and width configured to accommodate the elastic band 108. Thus, the width of opening 114 may be wider than the thickness of elastic band 108. The width of opening 114 may also accordingly be wider than the width of elastic band 108.

Cage 110 may include features configured to hold elastic band 108 when elastic band 108 is disposed within opening 114. For example, cage 110 may include protrusions 116 that aid in holding the elastic band 108 within the opening 114. The protrusions 116 may be, for example, teeth with triangular, square, or other geometries, depressions, adhesives, rods, and/or other types of protrusions or features that may aid in retaining elastic band 108 within opening 114. Protrusions 116 may be disposed within all or a portion of the opening 114. While the embodiment shown in FIG. 5 includes multiple triangular teeth shaped protrusions 116A-B and others, other embodiments may include protrusions and/or retaining features of other geometries and/or may include more or fewer protrusions.

Elastic band 108 may additionally include one or more openings 126A, and 126B. Various embodiments may include any number of such openings. The cage may include corresponding openings 118A and 118B. The openings 118A and 118B may be configured to correspond to the openings 126A and 126B so that, when elastic band 108 is disposed within opening 114, opening 118A is aligned with opening 126A, opening 118B is aligned with opening 126B, and so on. When openings 126A and 126B are aligned with openings 118A and 118B, respectively, fasteners may be disposed through each pair of openings to aid in holding the elastic band 108 within the opening 114 of the cage 110. In some examples, the fasteners may comprise removable fasteners such as pins, screws, bolts, brads, and/or the like.

In some examples, cage 110 may include a first segment and a second segment, which may be formed as a single piece during a manufacturing process. In some examples, the first segment is formed, elastic band 108 is placed such that openings 118A and 118B correspond to openings 126A and 126 B, and the second segment is formed such that molded protrusions and/or fingers permanently couple the first segment and the second segment to each other and to the elastic band. In some examples, elastic band 108 is placed within a mold (e.g., between two halves of the mold) and cage 110 is molded (e.g., over-molded, co-molded, double shot molded, etc.) such that the cage encloses an end portion of the elastic band.

Cage 110 may additionally include one or more detent(s) 120 and other features disposed on an exterior portion of cage 110. Such features may be configured to interface with a corresponding feature 124 disposed within opening 122. Detent(s) 120 may be, for example, one or more raised surfaces (e.g., protrusion) or depressions, fasteners, adhesives, or other features so that, when the elastic band 108 is pulled, detent(s) 120 and the corresponding feature 124 may form a mechanical interface (e.g., may include contacting walls) to hold the cage 110 within the opening 122. In some examples, detent(s) 120 includes springs and/or other biasing mechanisms such that detent(s) 120 may be depressed by a user such that the detent is flush with an external surface of cage 110, and may return to a raised position absent pressure applied by the user. The corresponding feature 124 within the opening 122 may include depressions to correspond to raised surfaces, raised surfaces to correspond to depressions, and/or corresponding fasteners or features. Thus, elastic band 108 may be more securely disposed within the opening 114.

Figure 6:
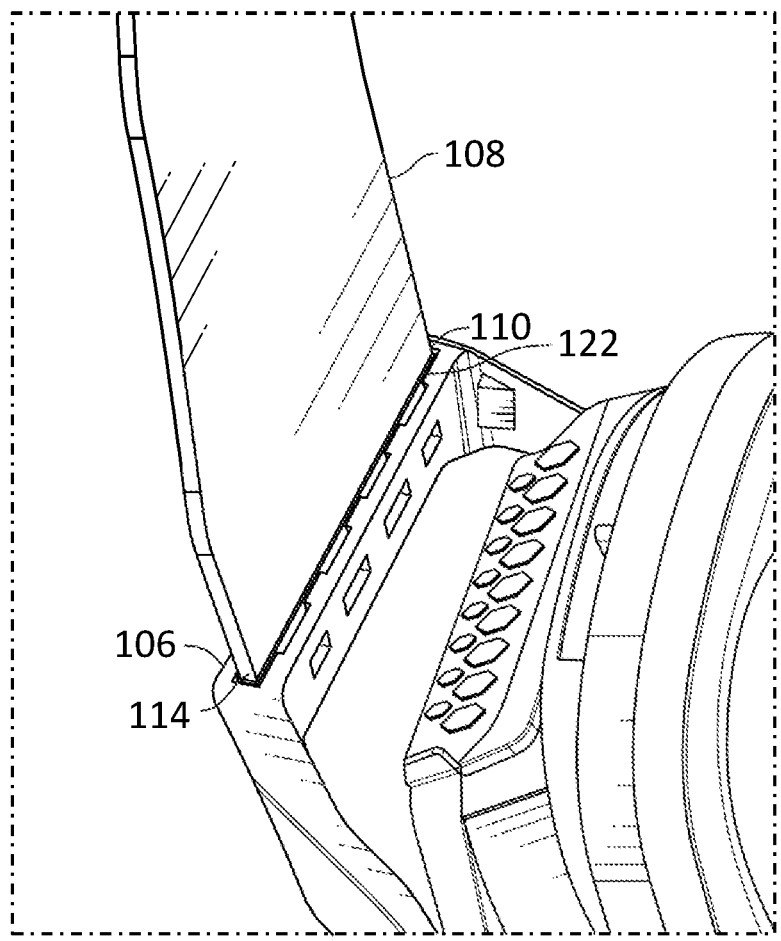
FIG. 6 is a partial isometric view of portions of the goggle of FIG. 1.

FIG. 6 shows a perspective view of a portion of the goggle of FIG. 1, in accordance with an embodiment of the present disclosure. FIG. 6 illustrates the cage 110 disposed within the opening 122 of the outrigger 106. As such, the cage 110 is coupled to the elastic band 108 and is disposed within the opening 122. The cage 110 may be held within the opening 122 through the features 124 as described herein. The elastic band 108 may also accordingly be held within the opening 114.

Figure 7:
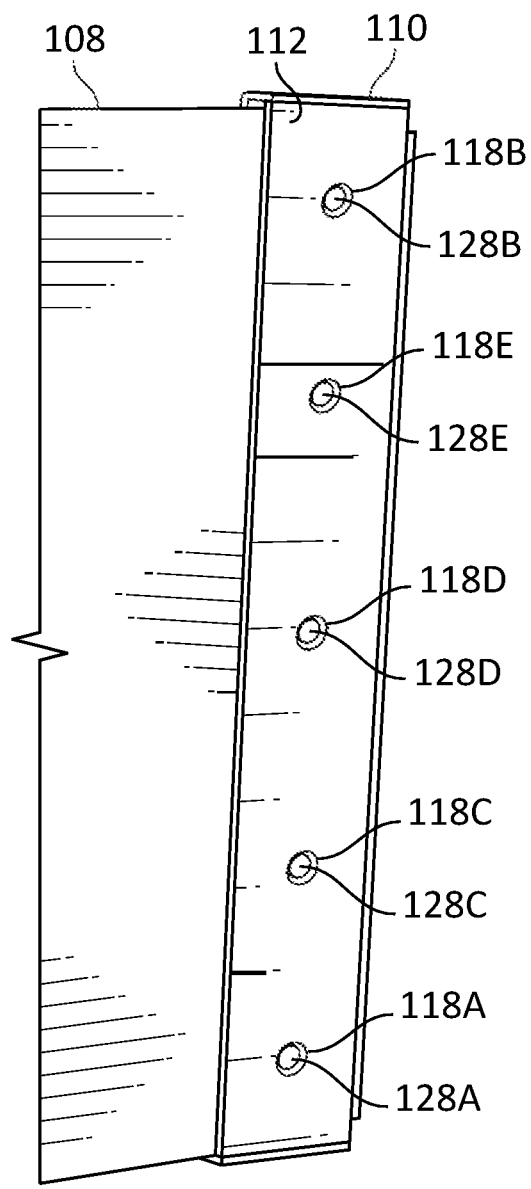
FIG. 7 is a front view of a strap and cage configured to be coupled to a goggle frame, in accordance with aspects of the present disclosure.
Figure 8:
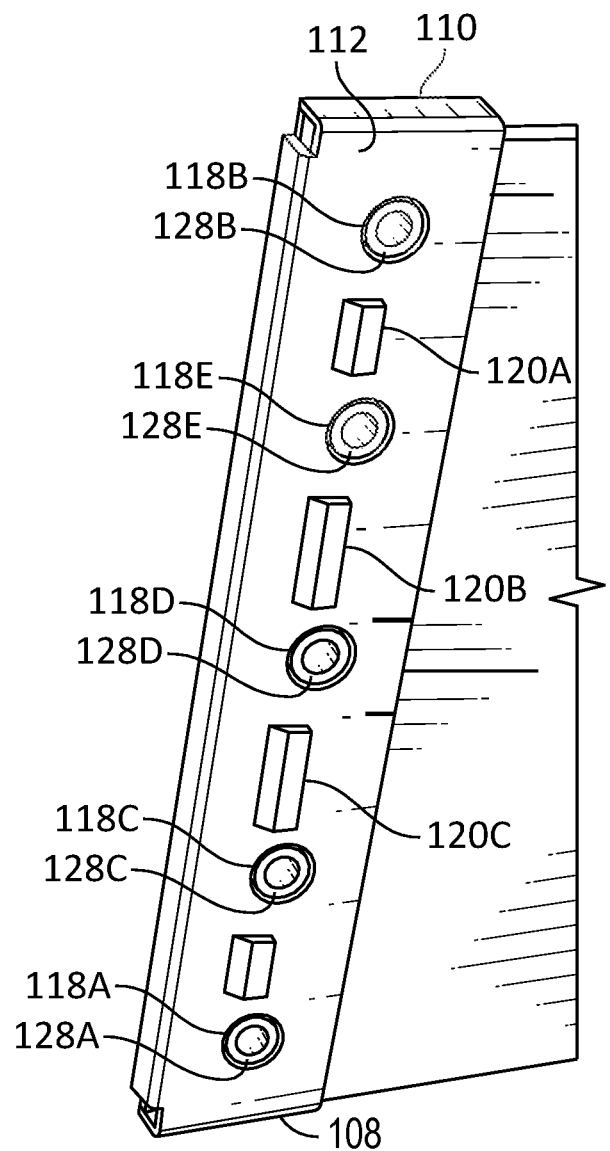
FIG. 8 is a rear view of the strap and cage of FIG. 7.

FIGS. 7 and 8 show views of a strap and cage configured to be coupled to a goggle frame, in accordance with embodiments of the present disclosure. FIGS. 7 and 8 show the elastic band 108 coupled to the cage 110. As shown, the cage 110 includes openings 118A-E. The elastic band 108 may include corresponding openings (e.g., openings 126A-E; not shown in FIGS. 7 and 8, but shown in FIG. 2). The openings 118A-E may be aligned with the openings 126A-E and fasteners 128A-E may be disposed through the openings 118A-E and 126A-E. As such, the fasteners 128A-E may aid in holding the elastic band 108 within the opening 114 of the cage 110.

In certain examples, the fasteners 128A-E may be, for example, a rivet, a mushroom cap, a bolt and/or a nut, a snap, a protrusion of the cage 110, a dowel, adhesive, teeth, and/or other type of feature configured to further secure the elastic band 108 within the opening 114 of the cage 110. In certain such examples, the openings 118A-E may be substantially (e.g., +/−20% in variance) evenly spaced on the cage 110. Thus, the distance between each of the openings 118A-E may be substantially similar. Furthermore, at least two of the openings 118A-E (e.g., the openings 118A and 118B) may be disposed on opposing sides of the cage 110. Disposing the openings in such a manner allows for more even distribution of stresses (e.g., resulting from pulling on the elastic band 108) within portions of the elastic band 108 and/or the cage 110, further increasing strength.

In FIG. 8 may illustrate another embodiment of the cage 110. FIG. 8 may illustrate detents 120A-E on an exterior surface of the cage 110. The detents 120A-E may be, for example, one or more raised surfaces (e.g., protrusion) or depressions, fasteners, adhesives, or other features configured to interface with corresponding features disposed within the opening 122 of the outrigger 106 and/or goggle frame 102. Such corresponding features may include depressions to correspond to raised surfaces, raised surfaces to correspond to depressions, and/or corresponding fasteners or other features. Detents 120A-E may allow for the cage 110 to be more securely disposed within the opening 114 and, thus, increase the strength of the coupling of the elastic band 108 to the goggle frame 102 and/or the outrigger 106. In some examples, one or more of detents 120A-E may comprise hooks configured to interface with depressions and/or recesses disposed within opening 122.

Figure 9:
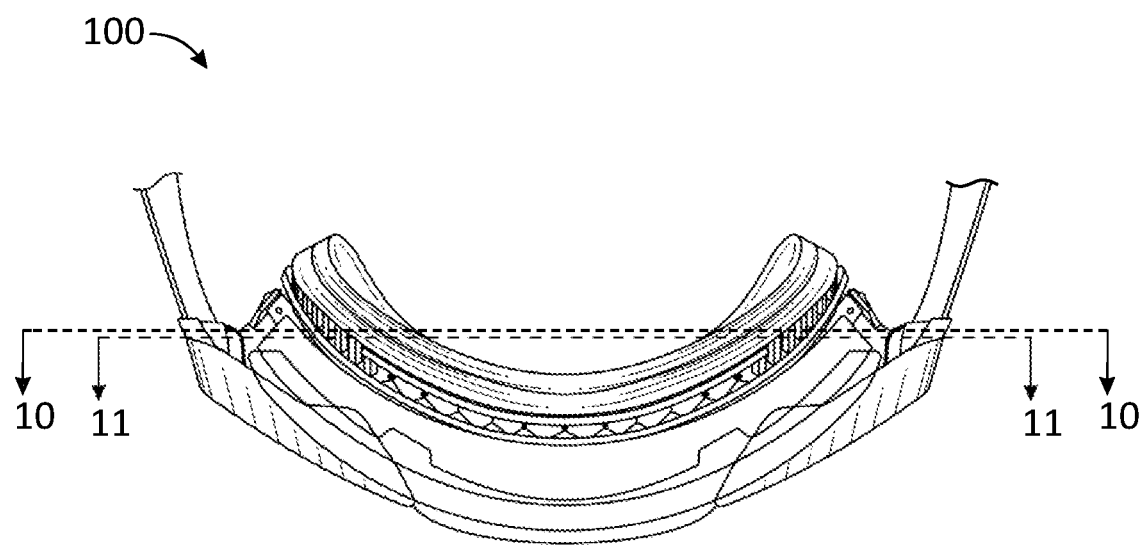
FIG. 9 is a top plan view of the goggle of FIG. 1.
Figure 10:
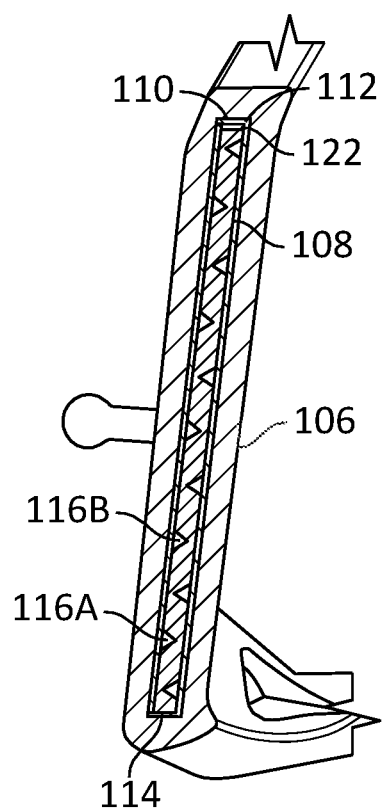
FIG. 10 is a first sectional view of the goggle of FIG. 9.
Figure 11:
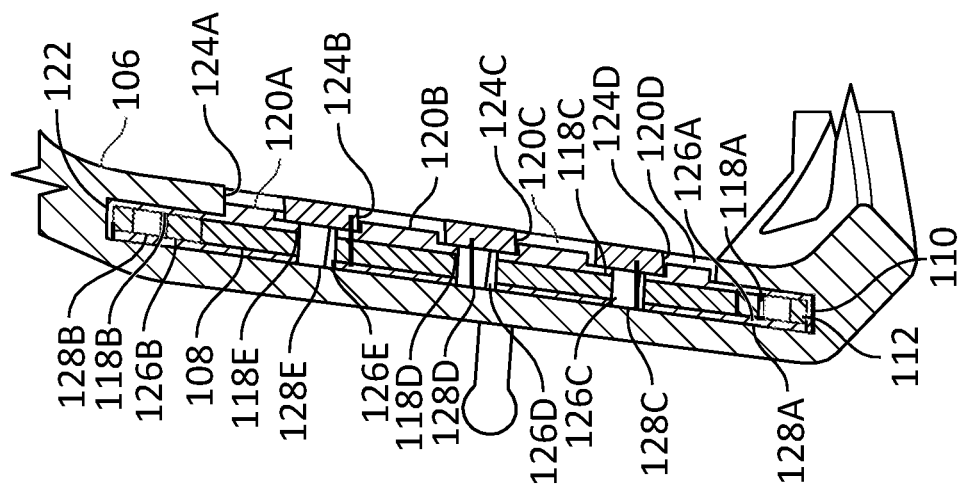
FIG. 11 is a second sectional view of the goggle of FIG. 9.

FIG. 9 shows a top view of the goggle of FIG. 1, in accordance with an embodiment of the present disclosure. FIG. 9 is a top view of the goggle 100. FIG. 9 shows planes 10-10 and 11-11. FIGS. 10 and 11 show cutaway views of the goggle of FIG. 9, in accordance with embodiments of the present disclosure. The cutaway view of FIG. 10 is taken along plane 10-10. The cutaway view of FIG. 11 is taken along plane 11-11.

The cutaway view of FIG. 10 illustrates the cage 110 disposed within opening 122 of the outrigger 106. As shown, the cage 110 may be substantially rectangular in cross-sectional shape and opening 122 may include a shape that corresponds to the cross-sectional shape of the cage 110 to hold the cage 110 within opening 122. The cutaway view of FIG. 10 further illustrates elastic band 108 disposed within opening 114 of the cage 110. While disposed within the opening 114, protrusions 116A and 116B, as well as other protrusions illustrated, may grip elastic band 108 to aid in holding elastic band 108 within opening 114. The protrusions may, for example, dig into the side of elastic band 108 to grip the elastic band 108.

The cutaway view of FIG. 11 illustrates that the detents 120A-D of the cage 110 are disposed within the features 124A-D. While certain embodiments of the features 124A-D may be depressions within the goggle frame 102 and/or outrigger 106, the embodiment shown in FIG. 11 illustrates that the features 124A-D may also be openings within the goggle frame 102 and/or the outrigger 106. The detents 120A-D may be disposed within at least a portion of the features 124A-D, respectively. The features 124A-D may include one or more surfaces to prevent the detents 120A-D (and, thus, the cage 110) from moving in one or more directions while disposed within the features 124A-D. Certain embodiments may constrain different directions of movement. Such directions may include a direction that prevents rearward movement of the cage 110 due to, for example, a pulling force exerted on the elastic band 108.

Additionally, as shown in FIG. 11, elastic band 108 may be coupled to the cage 110 through the fasteners 128A-E. Portions of fasteners 128A-E may be disposed within openings 118A-E of the cage 110 and openings 126A-E of elastic band 108 to couple the elastic band 108 to the cage 110.

Figure 12:
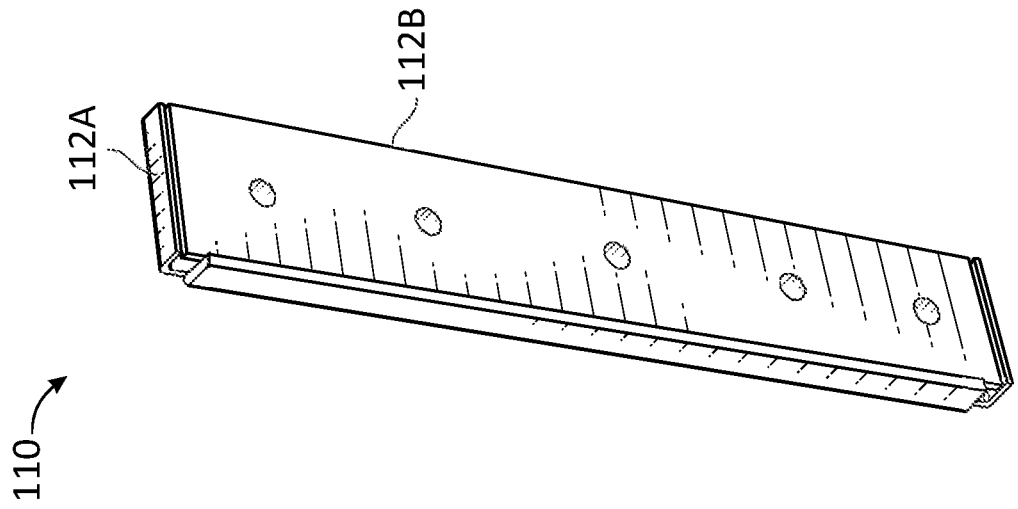
FIG. 12 is an isometric view of a cage in accordance with aspects of the present disclosure.

FIG. 12 shows a perspective view of a cage, in accordance with an embodiment of the present disclosure. FIG. 12 illustrates an embodiment of the cage 110. As shown in FIG. 12, the cage 110 may be made of a plurality of separate portions. That is, cage 110 may include cage bodies 112A and 112B. Each of cage bodies 112A and 112B may be, for example, a part manufactured from folded sheet metal, stamped sheet metal, machined stock, cast metal, molded composites, or other techniques. In certain embodiments, the cage bodies 112A and 112B may be made from separate techniques. In some examples, the cage bodies may be formed as a single piece (e.g., through co-molding, over-molding, etc.).

The separate cage bodies 112A and 112B may then be coupled together (e.g., friction fit, mechanically coupled, adhesively coupled, or coupled through other techniques) to form the cage 110. For example, in certain embodiments, the elastic band 108 may be disposed between the cage bodies 112A and 112B and the cage bodies 112A and 112B may then be accordingly coupled together to form the cage 110. The cage 110 may then be disposed within the opening 122.

B. Illustrative Method of Manufacturing a Cage Portion of a Goggle Outrigger

Figure 13:
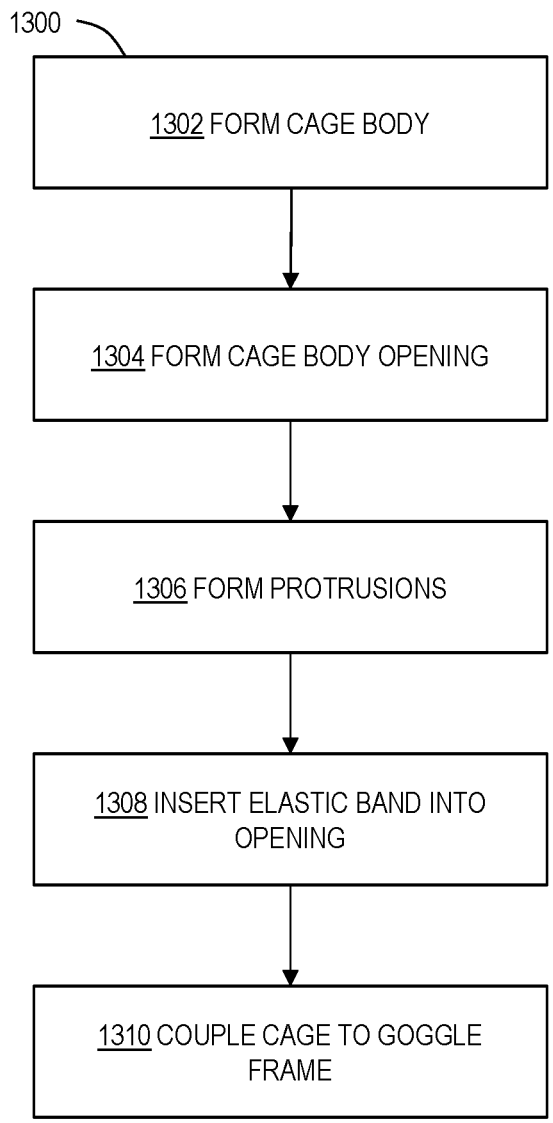
FIG. 13 is a flow chart depicting steps of an illustrative method for manufacturing the goggle of FIG. 1 or the goggle of FIG. 2 according to the present teachings.

This section describes steps of an illustrative method 1300 for manufacturing a cage portion of a goggle outrigger; see FIG. 13. Aspects of goggle 100 or goggle 200 may be utilized in the method steps described below. Where appropriate, reference may be made to components and systems that may be used in carrying out each step. These references are for illustration, and are not intended to limit the possible ways of carrying out any particular step of the method.

FIG. 13 is a flowchart illustrating steps performed in an illustrative method, and may not recite the complete process or all steps of the method. Although various steps of method 1300 are described below and depicted in FIG. 13, the steps need not necessarily all be performed, and in some cases may be performed simultaneously or in a different order than the order shown.

Step 1302 of method 1300 includes forming the cage body of the cage. The cage body may, in certain embodiments, be a metal cage body. The cage body may be formed from bent sheet metal (e.g., through one or more bending operations performed on a flat pattern), machined from stock, cast, molded, extruded, or otherwise appropriately formed.

Step 1304 of method 1300 includes forming the opening in the cage body. In certain embodiments, the opening may be formed when the cage body is formed. Thus, for example, in embodiments where the body is formed through bent sheet metal, bending of the sheet metal may accordingly form the opening. Furthermore, if the cage body is cast, the casting operation may form the opening at the same time as the cage body. In other embodiments, such as embodiments where the cage is machined or cast, the opening may be formed in a separate operation. Thus, for example, the opening may be machined into the cage body.

Step 1306 of method 1300 includes forming protrusions within the opening. For example, in embodiments where the opening and/or the cage body is formed from bent sheet metal, additional portions of the flat pattern may be bent to form the protrusions. Alternatively or additionally, the protrusions may be machined when the opening is machined. In other embodiments, the protrusions may be formed as a separate component and may be disposed within the opening and coupled to the cage body (e.g., through fasteners, adhesives, welding, or other techniques).

Step 1308 of method 1300 includes inserting the elastic band into the opening to couple the elastic band to the cage. In certain examples, inserting the elastic band into the opening includes holding the elastic band with the protrusions. In other embodiments, the elastic band may first be inserted onto a flat pattern or a partially formed opening. The opening may then be formed around the elastic band. Thus, for example, the elastic band may be disposed within a partially formed opening and the opening may then be finished around the elastic band by, for example, performing the remaining bending steps to form the opening. In such an example, the protrusions may be formed (e.g., bent) before the opening is fully formed. Thus, when the opening is fully bent, the protrusions may accordingly grasp the elastic band in a manner to retain the elastic band.

Step 1310 of method 1300 includes coupling the cage to the goggle frame and/or the outrigger. The cage may, thus, be inserted into an opening of the goggle frame and/or the outrigger. The cage may be held within the opening through features on the exterior of the cage and/or the opening of the goggle frame and/or the outrigger. In certain embodiments, coupling the cage to the goggle frame and/or the outrigger may include applying adhesive to the exterior of the cage and/or the opening of the goggle frame and/or the outrigger. Thus, for example, the opening and/or the cage may include a compressible coating that is configured to be deformed when the cage is disposed within the opening, further aiding in preventing the cage from separating from the opening.

C. Illustrative Method of Manufacturing and Using a Goggle

Figure 14:
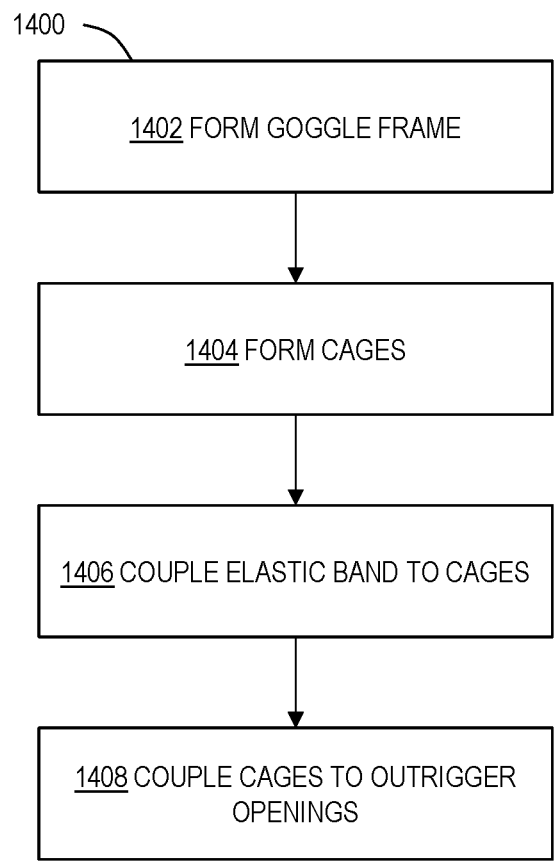
FIG. 14 is a flow chart depicting steps of an illustrative method for manufacturing and using the goggle of FIG. 1 or the goggle of FIG. 2 according to the present teachings.

This section describes steps of an illustrative method 1400 for manufacturing and using a goggle; see FIG. 14. Aspects of goggle 100 and goggle 200 may be utilized in the method steps described below. Where appropriate, reference may be made to components and systems that may be used in carrying out each step. These references are for illustration, and are not intended to limit the possible ways of carrying out any particular step of the method.

FIG. 14 is a flowchart illustrating steps performed in an illustrative method, and may not recite the complete process or all steps of the method. Although various steps of method 1400 are described below and depicted in FIG. 14, the steps need not necessarily all be performed, and in some cases may be performed simultaneously or in a different order than the order shown.

Step 1402 of method 1400 includes providing or forming a goggle frame, as described herein. In certain embodiments, the goggle frame and corresponding outriggers are formed separately and the outriggers are accordingly coupled to the goggle frame. Forming the goggle frame may include injection molding, blow molding, compression molding, extrusion molding, thermoforming, 3D-printing, and/or the like.

Step 1404 of method 1400 includes forming one or more cages as described herein. The one or more cages may be formed as described in method 1300. In some examples, the cage body may be formed from bent sheet metal (e.g., through one or more bending operations performed on a flat pattern), machined from stock, cast, molded, extruded, or otherwise appropriately formed.

Step 1406 of method 1400 may include coupling an elastic band to the one or more cages by, for example, inserting the elastic band into the opening of the cages. In certain examples, the elastic band may include a first end and a second end and the first end may be inserted into a first cage and the second end may be inserted into the second cage. Additionally, each cage may be composed of a plurality of portions. As such, the elastic band may be disposed within the plurality of portions and the portions may then be coupled together to form the cage and hold the end of the elastic band within the cage.

In some examples, steps 1404 and 1406 are performed at the same time, such as when these steps comprise over-molding of a plastic cage onto ends of the elastic band, with or without additional adhesive to secure the cage to the band.

Step 1408 of method 1400 may include coupling the one or more cages to openings of the goggle frame, or openings disposed within the outriggers, as described herein.

Step 1410 of method 1400 includes applying a force to the elastic band. The elastic band may stretch and exert a force on the coupling between the elastic band and the cage. Features of the cage (e.g., the protrusions) may hold the elastic band within the cage. The force may then be transferred to the opening through the cage. The cage may be held within the opening (e.g., through features of the cage such as the detents). As such, despite a force being exerted on the elastic band, the elastic band may remain coupled to the goggle frame through the cage.

D. Illustrative Method of Manufacturing a Goggle

Figure 15:
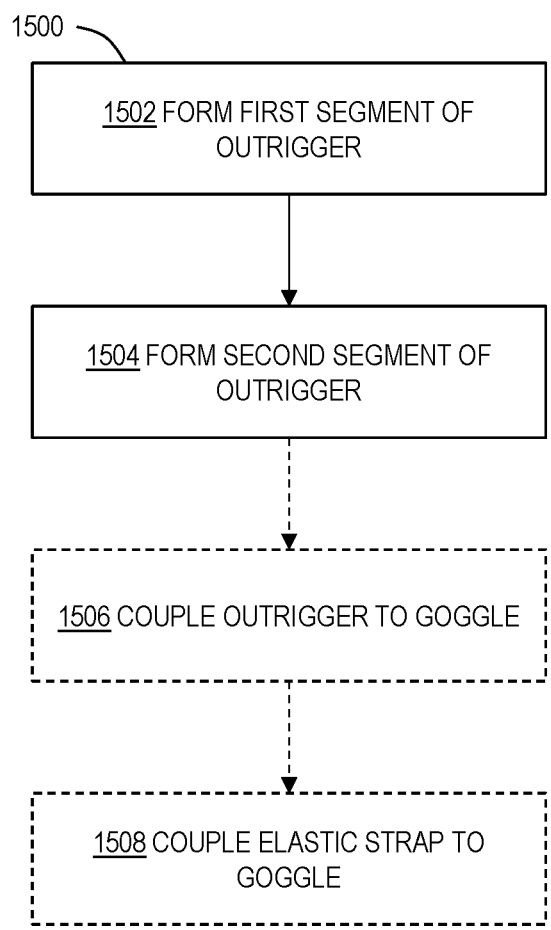
FIG. 15 is a flow chart depicting steps of an illustrative method for manufacturing the goggle of FIG. 2 according to the present teachings.

This section describes steps of an illustrative method 1500 for manufacturing a goggle; see FIG. 15. Aspects of goggle 200 or goggle 100 may be utilized in the method steps described below. Where appropriate, reference may be made to components and systems that may be used in carrying out each step. These references are for illustration, and are not intended to limit the possible ways of carrying out any particular step of the method.

FIG. 15 is a flowchart illustrating steps performed in an illustrative method, and may not recite the complete process or all steps of the method. Although various steps of method 1500 are described below and depicted in FIG. 15, the steps need not necessarily all be performed, and in some cases may be performed simultaneously or in a different order than the order shown.

Step 1502 of method 1500 includes forming a first segment of an outrigger, e.g., by injection molding. The first segment may be formed along with a goggle frame, such as by double shot molding, over-molding, or co-molding the goggle frame and the first segment of the outrigger together. In some examples, step 1502 includes molding (e.g., injection molding) the first segment, and including one or more joint-forming features (AKA joint features) 1620 on the first segment (see FIG. 16). For example, an end portion of the first segment may have a shape, such as one or more protrusions, channels, recesses, holes, keys, tails, pins, and/or the like. In some examples, the joint-forming feature(s) are configured to produce the first part (i.e., one "half") of a suitable male-female mating combination or interlock, such as a dovetail joint, a pin and socket joint, a tongue and groove, a mortise and tenon, etc. Molding the first segment may include injection molding, blow molding, compression molding, extrusion molding, or the like.

In some examples, step 1502 may include decoupling (e.g., breaking, cutting) one or more manufacturing artifacts from the first outrigger segment. In some examples, manufacturing the first segment of the outrigger includes flowing material through features such as a sprue and runners.

Figure 16:
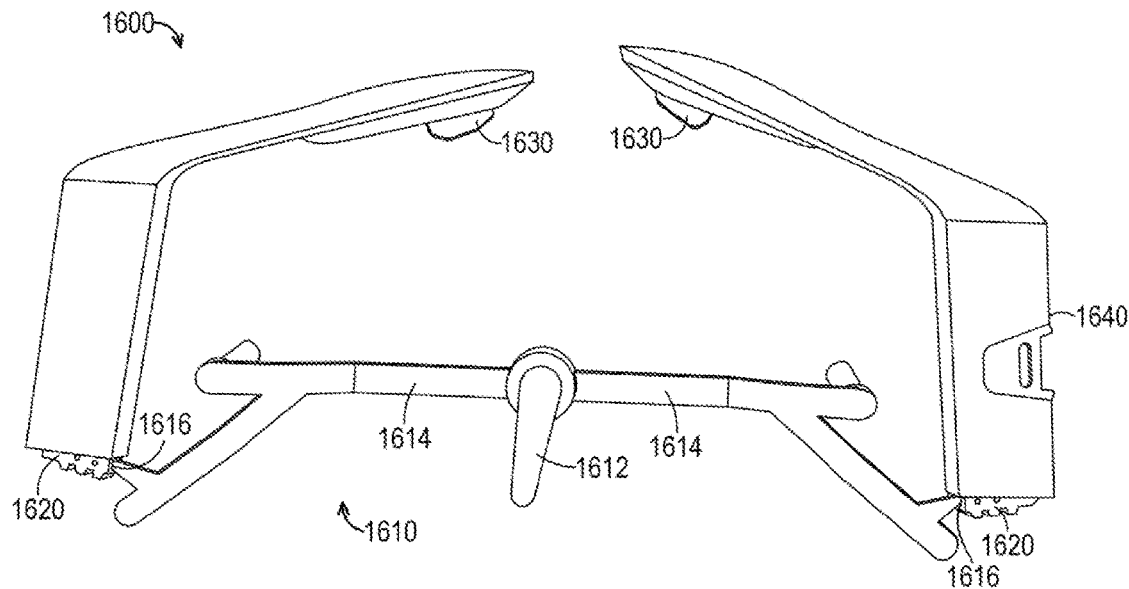
FIG. 16 is a front view of a pair of illustrative first outrigger segments after a first molding step.

As an illustrative example relating to step 1502, FIG. 16 depicts a pair of first outrigger segments 1600 coupled to manufacturing artifacts 1610 in the form of a sprue 1612 and runners 1614. First outrigger segments 1600 include two or more usable pieces, and runners 1614 couple the two or more pieces together during manufacturing. Here, decoupling the manufacturing artifacts from the first outrigger segments includes applying force (e.g., manually) to a joint 1616 between the first outrigger segments and runners 1614. In some examples, decoupling the manufacturing artifacts from the first outrigger segments includes any suitable powered method for separating two components, such as cutting, melting, and/or the like. In the depicted example, forming first outrigger segments includes forming tabs 1630 which are configured to couple the outrigger to a goggle frame, e.g., by snap-fit or friction fit in one or more slots or openings of the frame. In some examples, tabs 1630 include bent portions or hooks which are configured to interlock with apertures of the goggle frame. In some examples, forming the first segment of the outrigger includes forming openings 1640 (on the rear of the segment(s)) which are configured to receive a goggle strap. In some examples, forming the first segment of the outrigger includes forming only a part of opening 1640.

Step 1504 of method 1500 includes forming a second segment of the outrigger, e.g., by injection molding, such that the second segment is automatically fixed to at least a portion of the first segment to secure the first and second segments together. The second segment may be formed together with the goggle frame, such as by co-molding the goggle frame and the second segment of the outrigger together. The second segment may be molded, such as by injection molding, blow molding, compression molding, extrusion molding, or the like. In some examples, forming the second segment includes molding the second segment onto the first segment by flowing molten material into contact with the joint feature of the first segment, such that a permanent joint is automatically formed between the first segment and the second segment. In some examples, the permanent joint is a fixed joint configured as a single-use fastening mechanism. The second segment may be formed to the first segment to mechanically lock the first and second segments together (i.e., creating interlocking joint features). Features of the first segment may be configured to receive complementary material flow of the second segment therein, thereon, or therethrough to secure the second segment to the first segment. Forming the second segment of the outrigger to at least a portion of the first segment may include flowing material of the second segment through at least a portion of the first segment to mechanically lock the first and second segments together.

In some examples, step 1504 includes placing (or leaving) the first segment in a mold or holder, and injection molding the second segment such that material of the second segment flows onto, into, and/or over at least the one or more joint-forming features of the first segment. In some examples, one or more of the joint-forming features of the first segment includes one or more recesses or channels, and injection molding the second segment includes flowing molten material into the one or more recesses or tunnels. For example, this injection molding step may result in the automatic formation, on an end portion of the second segment, one or more complementary shapes corresponding to the protrusions, channels, recesses, holes, tails, pins, etc., on the first segment. In some examples, the joint-forming feature(s) are configured to produce the second part or "half" of the male-female mating combination (dovetail joint, pin and socket joint, mortise and tenon, tongue and groove, etc.). In some examples, molding the second segment of the outrigger automatically forms one or more shapes corresponding to the joint-forming features of the first segment.

In some examples, step 1504 may include decoupling (e.g., breaking, cutting) one or more manufacturing artifacts from the second outrigger segment. In some examples, manufacturing the second segment of the outrigger includes flowing material through features such as a sprue and runners.

Figure 17:
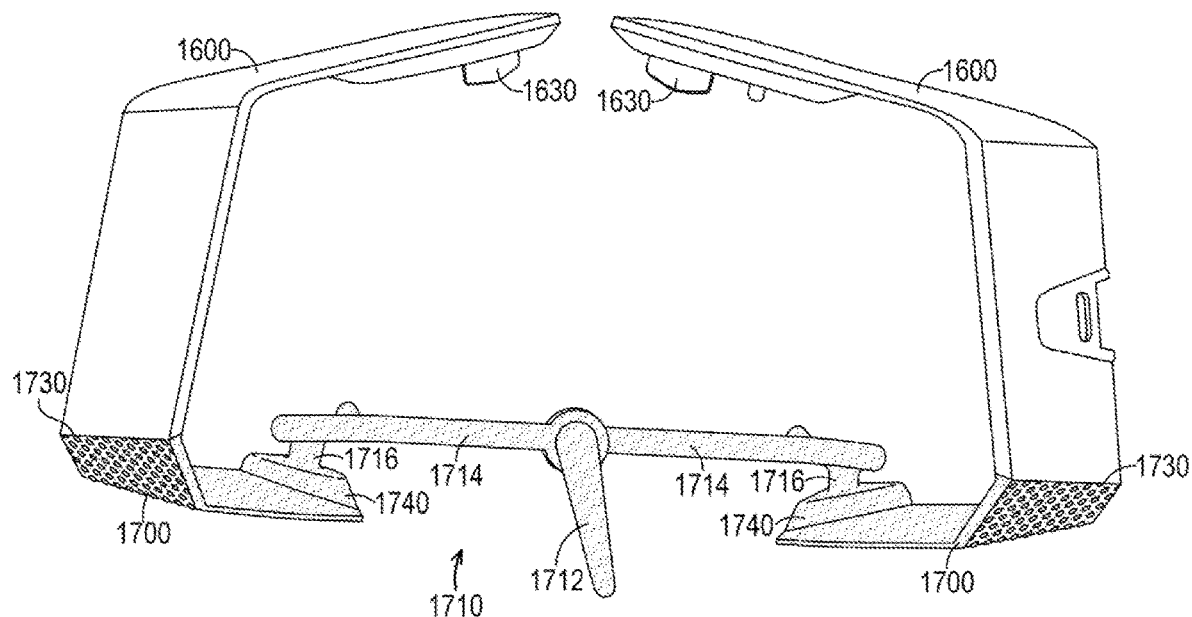
FIG. 17 is a front view of the pair of first outrigger segments after a second molding step has completed the outriggers by adding illustrative second segments to the first segments.

As an illustrative example relating to step 1504, FIG. 17 depicts a second pair of outrigger segments 1700 each molded onto one of the first outrigger segments 1600, and coupled to manufacturing artifacts 1710 in the form of a sprue 1712 and runners 1714. Second outrigger segments 1700 may include two or more usable pieces, and runners 1714 couple the two or more pieces together during manufacturing. In some examples, decoupling the manufacturing artifacts from the second outrigger segment includes applying force (e.g., manually) to a joint 1716 between the second outrigger segments and runners 1714. In some examples, decoupling the manufacturing artifacts from the second outrigger segments includes any suitable powered method for separating two components, such as cutting, melting, and/or the like.

Forming each second segment of the outrigger produces a seam or junction 1730 disposed between the first segment and the second segment. The junction depicted in the example of FIG. 17 is disposed adjacent a bottom end of a central leg of the outrigger, and the second segment of the outrigger includes a lower leg of the outrigger. However, the junction may be disposed in any suitable location (e.g., adjacent a top end of the central leg of the outrigger, at a midpoint of the outrigger, etc.). In some examples, the outrigger is substantially arcuate, and the junction is disposed at any point along the arc. In some examples, the outrigger comprises a central leg, a top leg coupled to a top end of the central leg, and a lower leg coupled to a bottom end of the central leg, and the junction is disposed at any corner between legs, or within any leg.

Forming the second segment of the outrigger may include forming tabs 1740 which are configured to couple the outrigger to a goggle frame, similar to tabs 1630. In some examples, tabs 1740 include bent portions or hooks which are configured to interlock with apertures of the goggle frame.

In some examples, forming the second segment of the outrigger includes forming a second part of receptacle or opening 1640, which is configured to receive a goggle strap.

Forming the first segment of the outrigger may include forming the first segment such that the first segment has a first material characteristic or property. Forming the second segment of the outrigger may include forming the second segment such that the second segment has a second material characteristic or property. The first material characteristic or property may be different than the second material characteristic or property. The first material characteristic may include a first color and/or a first material. The second material characteristic may include a second color and/or a second material. Examples of suitable material characteristics and color combinations are listed above (e.g., see Section A).

Step 1506 of method 1500 includes optionally coupling the outrigger to a goggle, e.g., to a frame of the goggle by attaching the first and second segments to the goggle. In some examples, coupling the outrigger to a goggle includes inserting tabs (e.g., tabs 1630, 1740) of the outrigger into apertures and/or recesses of the goggle frame. In some examples, coupling the outrigger to a goggle includes removably coupling end portions of the outrigger to a goggle using reversible detents, removable fasteners (e.g., screws, brads, pins, etc.), mating protrusions of the outrigger with apertures of the goggle or vice versa, and/or the like. In some examples, coupling the outrigger to a goggle includes permanently coupling end portions of the outrigger to a goggle by adhesive, melting, bonding, welding, and/or the like. In some examples, the first outrigger segment and the goggle frame are formed as a single piece, and coupling the outrigger to the goggle is performed during that operation.

Step 1508 of method 1500 includes optionally coupling an elastic strap to the outrigger. Steps 1508 and 1506 may be performed in any order. In some examples, coupling the elastic strap to the outrigger includes inserting a cage coupled (e.g., integrally coupled, such as by over-molding) to an end of the elastic strap into a receptacle (e.g., opening 1640) disposed in a lateral portion of the outrigger. In some examples, a portion of the opening is included within the first segment, and a remaining portion of the opening is included within the second segment. In some examples, the cage includes a hook or other feature configured to mate with a complementary aperture or recess of the opening. In some examples, inserting the cage into the aperture includes slightly depressing the hook and/or deforming the opening, such that the hook snaps into the recess or aperture when the cage is inserted.

Additional examples of manufacturing methods of the present disclosure, as well as embodiments of steps described above, are laid out below. These are presented without limitation as a series of labeled paragraphs.

E0. A method for manufacturing a sport goggle, the method comprising:
   molding a first segment of an outrigger such that an end portion of the first segment includes a joint feature; and
   molding a second segment of the outrigger onto the first segment by flowing molten material into contact with the joint feature, such that a permanent joint is automatically formed between the first segment and the second segment.

E1. The method of paragraph E0, wherein the outrigger is a C-shaped structure and the first and second segments are disposed end-to-end, such that the outrigger extends continuously from the first segment to the second segment.

E2. The method of paragraph E1, wherein the joint is disposed at a lower corner of the outrigger.

E3. The method of any of paragraphs E0 through E2, further comprising coupling the outrigger to a goggle frame by attaching the first and second segments to the goggle frame, such that a gap is formed between the outrigger and a lateral side of the goggle frame.

E4. The method of paragraph E3, wherein forming the first segment of the outrigger includes forming a first tab, wherein forming the second segment of the outrigger includes forming a second tab, and wherein coupling the outrigger to the goggle frame includes inserting the first tab into a first aperture of the goggle frame and inserting the second tab into a second aperture of the goggle frame.

E5. The method of any of paragraphs E0 through E4, further comprising coupling an elastic strap to the outrigger.

E6. The method of paragraph E5, wherein the elastic strap includes a cage over-molded onto an end of the elastic strap, and coupling the elastic strap to the outrigger includes inserting the cage into a receptacle formed in the outrigger.

E7. The method of paragraph E6, further comprising molding the receptacle of the outrigger partially in the first segment and partially in the second segment.

E8. The method of any of paragraphs E0 through E7, wherein molding the first and second segments comprises injection molding.

E9. The method of any of paragraphs E0 through E8, wherein the joint feature includes one or more recesses in the first segment, into which the molten material is flowed when molding the second segment.

E10. The method of paragraph E9, wherein the joint feature of the first segment is one part of a male/female mating combination.

E11. The method of any of paragraphs E0 through E10, wherein the first segment has a first material characteristic, and wherein the second segment has a second material characteristic different from the first material characteristic.

F0. A method for manufacturing a sport goggle, the method comprising:
   injection molding a first segment of an outrigger of a goggle; and
   injection molding a second segment of the outrigger by flowing molten material into contact with an end of the first segment, such that a fixed joint is automatically formed at a junction between the first and second segments;
   wherein the end-to-end first and second segments combine to extend an entire length of the outrigger.

F1. The method of paragraph F0, wherein the end of the first segment has a first shape, and molding the second segment of the outrigger automatically forms an interlocking second shape when forming the fixed joint.

F2. The method of paragraph F1, wherein the fixed joint comprises a male-female joint.

F3. The method of paragraph F2, wherein the fixed joint is a mortise and tenon joint.

F4. The method of any of paragraphs F0 through F3, wherein molding the first and second segments of the outrigger includes forming tabs configured to couple the outrigger to a frame of the goggle.

F5. The method of paragraph F4, further comprising:
   forming a receptacle in the outrigger; and
   coupling an elastic strap to the outrigger by inserting an over-molded cage of the elastic strap into the receptacle of the outrigger.

F6. The method of any of paragraphs F0 through F5, wherein the first segment has a first material characteristic, and wherein the second segment has a second material characteristic different from the first material characteristic.

F7. The method of any of paragraphs F0 through F6, wherein the outrigger is a continuous C-shaped structure, and the fixed joint is disposed at a lower corner of the outrigger.

E. Illustrative Combinations and Additional Examples

This section describes additional aspects and features of goggles and related methods, presented without limitation as a series of paragraphs, some or all of which may be alphanumerically designated for clarity and efficiency. Each of these paragraphs can be combined with one or more other paragraphs, and/or with disclosure from elsewhere in this application, including the materials incorporated by reference in the Cross-References, in any suitable manner. Some of the paragraphs below expressly refer to and further limit other paragraphs, providing without limitation examples of some of the suitable combinations.

A0. A goggle comprising: a goggle frame; and an outrigger disposed on an end of the goggle frame, the outrigger comprising: a first segment comprising a first material characteristic; and a second segment secured to the first segment, the second segment comprising a second material characteristic.

A1. The goggle of A0, wherein the first material characteristic is different than the second material characteristic.

A2. The goggle of A0 or A1, wherein the second segment is molded to the first segment to secure the first segment and the second segment together.

A3. The goggle of any one of paragraphs A0 through A2, wherein the first and second segments comprise complementary interlocking features that mechanically bond the first segment and the second segment together.

A4. The goggle of A3, wherein material flow of one of the first segment and the second segment through the other of the first segment and the second segment mechanically bonds the first segment and the second segment together.

A5. The goggle of A4, wherein: the one of the first segment and the second segment comprises one or more tunnels; and material flow of the other of the first segment and the second segment through the one or more tunnels permanently bonds the first segment and the second segment together.

A6. The goggle of A3, wherein the first segment and the second segment include complementary shapes that interlock together to secure the first segment and the second segment together.

A7. The goggle of A6, wherein the complementary shapes create a solid friction lock securing the first segment and the second segment together.

B0. An outrigger system for a goggle, the outrigger system comprising: a first segment comprising a first material characteristic; and a second segment secured to the first segment and comprising a second material characteristic different than the first material characteristic.

B1. The outrigger system of B0, wherein: the first material characteristic is a first material; and the second material characteristic is a second material different than the first material.

B2. The outrigger system of B1, wherein the second material is molded to the first segment to secure the first segment and the second segment together.

B3. The outrigger system of B2, wherein material flow of the second material through and/or onto portions of the first segment mechanically bonds the first segment and the second segment together.

B4. The outrigger system of B2, wherein: the first material is a thermoplastic polyurethane; and the second material is a thermoplastic elastomer.

B5. The outrigger system of any one of paragraphs B0 through B4, wherein: the first material characteristic includes a first texture; and the second material characteristic includes a second texture different than the first texture.

C0. A method of manufacturing a goggle, comprising: forming or providing a goggle frame; forming a first segment of an outrigger of the goggle frame; forming a second segment of the outrigger to at least a portion of the first segment to secure the first segment and the second segment together.

C1. The method of C0, wherein forming the second segment to at least a portion of the first segment comprises mechanically locking the first segment and the second segment together.

C2. The method of C1, wherein: forming the first segment comprises forming one or more interlocking features of the first segment; and forming the second segment comprises flowing material of the second segment in or through the one or more features of the first segment to mechanically lock the first segment and the second segment together.

C3. The method of any one of paragraphs C0 through C2, wherein: forming the first segment comprises forming the first segment with a first material characteristic; and forming the second segment comprises forming the second segment with a second material characteristic different than the first material characteristic of the first segment.

C4. The method of any one of paragraphs C0 through C3, wherein at least one of the first segment and the second segment is formed as a single piece with the goggle frame.

D0. A goggle comprising: a goggle frame; and a C-shaped outrigger coupled to the goggle frame, the outrigger including: a first segment extending along and defining a first portion of the C-shape; and a second segment extending along and defining a remaining portion of the C-shape; wherein the first segment and the second segment are integrally coupled at a discrete joint.

D1. The goggle of paragraph D0, further comprising an elastic strap coupled to the outrigger.

D2. The goggle of paragraph D0 or D1, wherein the joint is disposed adjacent a bottom portion of a central leg of the outrigger.

D3. The goggle of any of paragraphs D0 through D2, wherein the first segment has a first material characteristic, and wherein the second segment has a second material characteristic different from the first material characteristic.

D4. The goggle any of paragraphs D0 through D3, wherein portions of the first segment interlock with complementary portions of the second segment.

Advantages, Features, and Benefits

The different embodiments and examples of the goggle described herein provide several advantages over known solutions. For example, illustrative embodiments and examples described herein allow individual outriggers to include a plurality of materials having different material properties.

Additionally, and among other benefits, illustrative embodiments and examples described herein improve structural integrity of component junctions disposed within goggle outriggers.

Additionally, and among other benefits, illustrative embodiments and examples described herein decrease goggle sizes by including a more compact goggle-elastic band interface.

Additionally, and among other benefits, illustrative methods described herein provide greater flexibility to customize ornamental and/or functional features of the outriggers in ways that are unavailable in single-piece outrigger manufacturing. In other words, a greater number of appearance and functionality options are available when designing outriggers of the present disclosure.

No known system or device can perform these functions. However, not all embodiments and examples described herein provide the same advantages or the same degree of advantage.

CONCLUSION

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

The invention claimed is:

1. A method of manufacturing a goggle, the method comprising:
   clamping a cage onto an end of an elastic band by bending sheet metal of the cage to form a plurality of walls defining an internal volume and a cage opening on only one side, such that the plurality of walls surround the end of the elastic band and the elastic band extends through the opening;
   aligning a hole in the elastic band with respective openings in each of a pair of the walls of the cage, such that the hole and the openings are in register with each other; and
   inserting a fastener through the hole in the elastic band and through the openings in the pair of cage walls.

2. The method of claim 1, further comprising bending a plurality of tabs of the sheet metal to form protrusions configured to extend into the internal volume, such that clamping the cage onto the end of the elastic band causes the protrusions to contact the elastic band and aid in retaining the end of the elastic band within the cage.

3. The method of claim 2, wherein the protrusions extend orthogonally from one or more of the walls of the cage.

4. The method of claim 1, wherein the cage comprises a first piece of the sheet metal and a second piece of the sheet metal, and clamping the cage onto the end of the elastic band comprises:
   disposing the first piece of sheet metal on one side of the elastic band;
   disposing the second piece of sheet metal on an opposing side of the elastic band and folding a tab portion of the second piece of sheet metal over an edge of the elastic band toward the first piece of sheet metal.

5. The method of claim 1, further comprising:
   securing the end of the elastic band to a goggle by inserting the cage into a receptacle of the goggle.

6. The method of claim 5, wherein the receptacle of the goggle is disposed in an outrigger of the goggle.

7. The method of claim 6, wherein the sheet metal of the cage has a higher modulus of elasticity than a material of the outrigger.

8. The method of claim 5, wherein the receptacle is a blind hole.

9. The method of claim 5, further comprising mating a male detent feature of the cage with a corresponding female feature of the receptacle to retain the cage in the receptacle.

10. The method of claim 1, wherein the elastic band is a flat elastic band configured to secure the goggle when in use by wrapping around a head of a user.

11. A method of manufacturing a goggle, the method comprising:
    clamping a cage onto an end of an elastic band by bending sheet metal of the cage to form a plurality of walls defining an internal volume and a cage opening on only one side, such that the plurality of walls surround the end of the elastic band and the elastic band extends through the opening;
    securing the end of the elastic band to a goggle by inserting the cage into a receptacle of the goggle; and
    mating a male detent feature of the cage with a corresponding female feature of the receptacle to retain the cage in the receptacle.

12. The method of claim 11, further comprising bending a plurality of tabs of the sheet metal to form protrusions configured to extend into the internal volume, such that clamping the cage onto the end of the elastic band causes the protrusions to contact the elastic band and aid in retaining the end of the elastic band within the cage.

13. The method of claim 12, wherein the protrusions extend orthogonally from one or more of the walls of the cage.

14. The method of claim 11, wherein the cage comprises a first piece of the sheet metal and a second piece of the sheet metal, and clamping the cage onto the end of the elastic band comprises:
    disposing the first piece of sheet metal on one side of the elastic band;
    disposing the second piece of sheet metal on an opposing side of the elastic band and folding a tab portion of the second piece of sheet metal over an edge of the elastic band toward the first piece of sheet metal.

15. The method of claim 11, further comprising:
    aligning a hole in the elastic band with respective openings in each of a pair of the walls of the cage, such that the hole and the openings are in register with each other; and
    inserting a fastener through the hole in the elastic band and through the openings in the pair of cage walls.

16. The method of claim 11, wherein the receptacle of the goggle is disposed in an outrigger of the goggle.

17. The method of claim 16, wherein the sheet metal of the cage has a higher modulus of elasticity than a material of the outrigger.

18. The method of claim 11, wherein the receptacle is a blind hole.

19. The method of claim 11, wherein the elastic band is a flat elastic band configured to secure the goggle when in use by wrapping around a head of a user.

* * * * *